United States Patent [19]
Wortrich

[11] Patent Number: 5,364,365
[45] Date of Patent: Nov. 15, 1994

[54] SAFETY DEVICE FOR LAPAROSCOPIC INSTRUMENTS

[75] Inventor: Theodore S. Wortrich, Long Beach, Calif.

[73] Assignee: Surgin Surgical Instrumentation, Inc., Tustin, Calif.

[21] Appl. No.: 114,207

[22] Filed: Aug. 30, 1993

[51] Int. Cl.⁵ .......................................... A61M 5/178
[52] U.S. Cl. ................................ 604/158; 604/164; 606/185
[58] Field of Search ............... 604/117, 158, 164, 165, 604/171; 606/185

[56] References Cited

U.S. PATENT DOCUMENTS

| | | |
|---|---|---|
| 2,623,521 | 12/1952 | Shaw . |
| 2,630,803 | 3/1953 | Baran . |
| 3,540,447 | 11/1970 | Howe . |
| 4,144,884 | 3/1979 | Tersteegen et al. . |
| 4,254,762 | 3/1981 | Yoon . |
| 4,535,773 | 8/1985 | Yoon . |
| 4,654,030 | 3/1987 | Moll et al. ............... 604/165 |
| 4,828,547 | 5/1989 | Sahl et al. . |
| 4,869,717 | 9/1989 | Adair . |
| 4,931,042 | 6/1990 | Holmes et al. . |
| 5,030,206 | 7/1991 | Lander ................... 606/185 |
| 5,066,288 | 11/1991 | Deniega et al. . |
| 5,104,382 | 4/1992 | Brinkerhoff et al. . |
| 5,114,407 | 5/1992 | Burbank . |
| 5,116,353 | 5/1992 | Green . |
| 5,127,909 | 7/1992 | Shichman ............... 604/165 |
| 5,129,885 | 7/1992 | Green et al. . |
| 5,137,509 | 8/1992 | Freitas . |
| 5,226,426 | 7/1993 | Yoon ....................... 604/165 |

*Primary Examiner*—Jerome L. Kruter
*Attorney, Agent, or Firm*—Merchant, Gould, Smith, Edell, Welter & Schmidt

[57] ABSTRACT

A thin bodied elongated surgical instrument for penetrating into a body cavity and thereafter being useful for performing surgical functions disposes an obturator within a cutting cannula. The obturator is spring mounted to retract within the cannula in response to resistance encountered at a body wall, but moves to an extended distal position inside the body cavity. In that position the obturator is manually or automatically locked in axial position, so that means at the extended end can be used in the surgical procedure without danger of cutting internal tissue or organs. This safety device facilitates initial insertion of an insufflation needle, and subsequent insertion and use of other instruments during laparoscopic surgery.

14 Claims, 8 Drawing Sheets

SAFETY DEVICE FOR LAPAROSCOPIC INSTRUMENTS

FIELD OF THE INVENTION

This invention relates to laparoscopic instruments and procedures, and more particularly, to devices for minimizing the risk of inadvertent incision or penetration of internal organs in such procedures.

BACKGROUND OF THE INVENTION

In endoscopic or laparoscopic surgery, various instruments are inserted through the skin and body wall into a body cavity wherein surgical procedures are to be undertaken. The interior operating site is "visualized" (viewed) using an endoscope or viewing port that also extends into the body cavity. Viewing the cavity interior, a surgeon can conduct operative procedures using different narrow instruments with significantly less trauma than conventional invasive surgery, thus also leading to typically much shorter recovery times for the patient.

To permit better visualization of the internal body cavity, to permit easier access to the operative site, and to reduce the danger of inadvertent engagement with interior organs or tissue, an "insufflation" procedure is first employed. In this procedure a clear fluid, typically carbon dioxide, is injected under pressure into the body cavity to initiate its enlargement and maintain it in the enlarged form.

In order to insufflate, however, a small instrument must be inserted first without visual guidance. After a small incision is made, a thin pneumoperitoneum insufflation needle (called a Veress type needle) or the like is used to puncture the cavity wall and the gas is introduced through the needle. The gas pressure distends the cavity and allows larger implements such as a trocar to enter at a lower risk of injury to internal organs so that the required instrument or instruments can then be inserted. The term "trocar" is sometimes used to refer to a cannula having a cutting edge, and sometimes to a cutting blade within a cannula. It will be employed here in the generic sense. Insufflation needles are comprised of an inner tube with a blunt end and an outer cutting cannula, the inner tube being movable within the outer cannula and spring biased so as to retract into the outer cannula to allow cutting to take place as long as physical resistance is encountered. When penetration is complete, however, the inner cannula extends beyond the cutting edge, exposing a side orifice in the inner cannula through which the gas will flow to create the pneumoperitoneum. A recognized problem in this arrangement is that the inner element retracts into the outer cannula whenever the needle comes in contact with internal vital organs or tissue, thereby exposing the cutting edge and possibly causing further penetration or injury.

In recognition of these problems, various safety devices for laparoscopic instruments have been devised. In U.S. Pat. No. 4,254,762, for example, an endoscope tube is seated within a hollow needle-like trocar and arranged to snap outwardly when the puncture through the body wall has been completed. This is done to enable the trocar and endoscope functions to be combined, so the procedure does not require separate penetrations by a trocar and then an endoscopic instrument. However, "blind" insertion of the insufflation needle is still required, and the danger of inadvertent contact with organs or tissues still remains. Furthermore, the cutting edge of the cannula is still unprotected, because the protruding tip of the endoscope is withdrawn relative to the cutting edge if some resistance is encountered.

In U.S. Pat. No. 5,104,382 a cylindrical hollow element with a cutting end (called an "obturator" in the patent) encompasses an interior rod (called a shield) with a blunt end that is spring loaded in the distal direction. Both the "obturator" and the inner "shield" are within a larger cannula that is also forced through the body wall as the cutting tip penetrates. The blunt end protects temporarily against interior cutting only to the extent of the spring force after the body cavity is reached, and both the "obturator" and "shield" are withdrawn through the cannula at that time.

A different approach is employed in the safety trocar of U.S. Pat. No. 5,116,353, in which a center cutter must encounter resistance, or be withdrawn into the cannula in which it moves. In another patent, U.S. Pat. No. 5,137,509, the surgeon is able to view the relative position of the cylindrical members during penetration, by what is termed an "enhanced visual indicator." Yet another safety puncturing instrument is disclosed in U.S. Pat. No. 4,535,773. In this instrument the point of an implement centrally disposed within a cannula becomes protected by an inner sleeve between the cannula and the implement, which moves out beyond the cutting tip whenever penetration is completed.

The foregoing systems do not provide a satisfactory answer to the problem of enhancing protection for a very small insufflation needle or other device which is to be used during a laparoscopic or endoscopic procedure. Inherently, the insufflation must be undertaken in the "blind" procedure, since insufflation precedes insertion of a viewing instrument. At other times, moreover, it is desired to insert a separate instrument of small diameter, as for purposes of manipulating sutures or other small elements within the body cavity. It is desirable to penetrate such instruments through the body wall and then to employ the instrument immediately, and in a safe fashion. Thus a functional terminal portion on a thin cutting instrument can be very useful, as with an insufflation needle, so that the inserted device can both penetrate into the cavity and be used for some operative function thereafter.

SUMMARY OF THE INVENTION

The objective of penetrating a needle-like functional instrument through a body wall and thereafter insuring that the cutting edge does not directly encounter organs or tissues is met by incorporating an obturator rod having a blunt, functional end that is slidably mounted within a sleeve having a distal cutting end. The rod is spring mounted within a handle controlled by the surgeon, and is biased under light force in the distal direction, and lockable in an extended position automatically, or by the surgeon, using control means at the handle. Thus, after insertion and locking only the blunt fixed end encounters organs or tissue if there is an inadvertent placement of the needle. A viewing window can be included in the handle to enable the rod position to be visually checked.

In one example of the device in accordance with the invention, a valve system coupled to the handle provides a flow of carbon dioxide or other gas to an interior conduit along the length of the rod, which has a side orifice for insufflation purposes. A control button is mounted on the handle, and the surgeon can press the button inwardly to maintain the rod free to retract axially against the spring bias when resistance is encountered. When penetration is complete and the blunt end extends, however, the surgeon can simply release the button to lock the blunt end in its extended position, following which the insufflation needle can be utilized for its intended purpose.

Alternatively, the thin hollow cutting instrument can incorporate a central obturator rod having a blunt end configured with an open-sided, transverse eyelet. Once within the cavity, the central rod is locked in place and the functional tip can be used as a suture retriever manipulator, irrigation/aspiration device, or for other purposes. Consequently, the surgeon has a procedure available that can be used to augment a planned sequence of steps or confront unexpected situations, since it is often desirable to enter a body cavity from a different angle or location or to insert a special instrument.

There is some preference for an instrument in which the obturator element automatically locks into place after the tip has reached the body cavity. A device for this purpose incorporates an obturator rod with a functional tip reciprocal within a cannula having a cutting edge, the proximal end of the rod being engaged by a spring which biases the obturator in the distal direction. An arming mechanism in the handle, controlled by the surgeon, may be set to maintain a locking mechanism out of operative relationship with the reciprocal rod. Thus, when encountering resistance, the obturator is withdrawn into the cannula, allowing the cutting edge to penetrate through tissue. However, having passed the body wall and being freed of the tissue, the obturator moves toward its distal limit, at which position the arming mechanism is disengaged and the lock secures the obturator against withdrawal into the cannula.

The distal end of the cannula can be varied to effect a number of different separate functions, such as serving as an irrigation/aspiration tip, a cauterizer or a suture cutter.

BRIEF DESCRIPTION OF THE DRAWINGS

A better understanding of the invention may be had by reference to the accompanying drawings, taken in conjunction with the following description, in which.

DETAILED DESCRIPTION OF THE INVENTION

An improved Veress needle device 10, arranged as a safety instrument for laparoscopic applications, is shown in FIGS. 1-6, to which reference is now made. A cannula 12 comprising a long, thin, hollow cylinder extending along a central axis is of a selected outer diameter, typically in the order of 2-10 mm. The cannula 12 has a slanted distal cutting end 14. Within the cannula 12, a functional obturator rod 16, here serving as a Veress needle, is mounted to be bidirectionally reciprocal. The obturator 16 is a hollow rod having a blunt distal tip 18 and including a side aperture 20 communicating with the interior conduit within the obturator 16.

Figure 1:
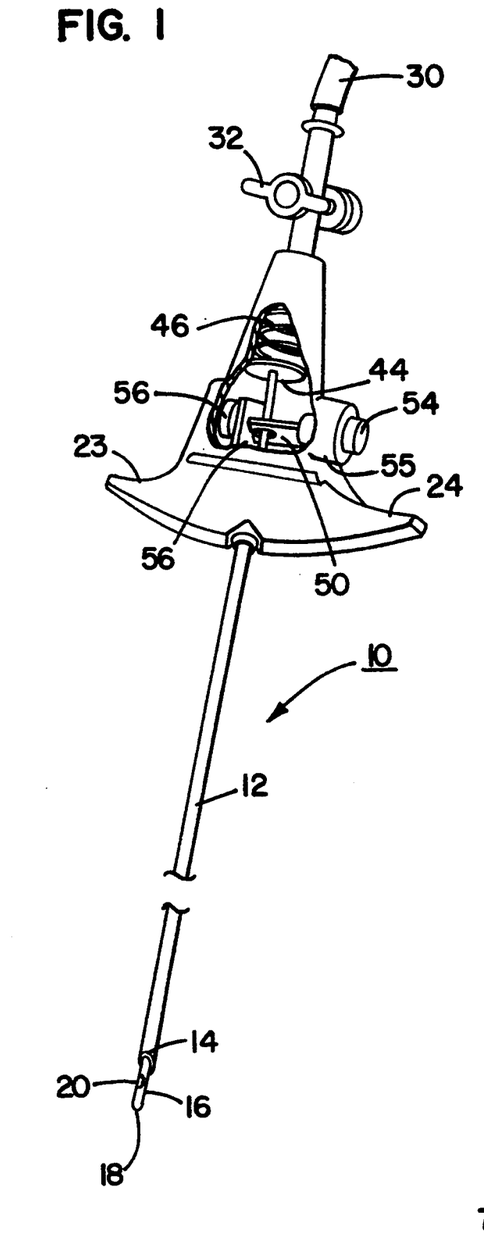
FIG. 1 is a perspective view, partially broken away, of a safety device for a Veress needle instrument in accordance with the invention.
Figure 2:
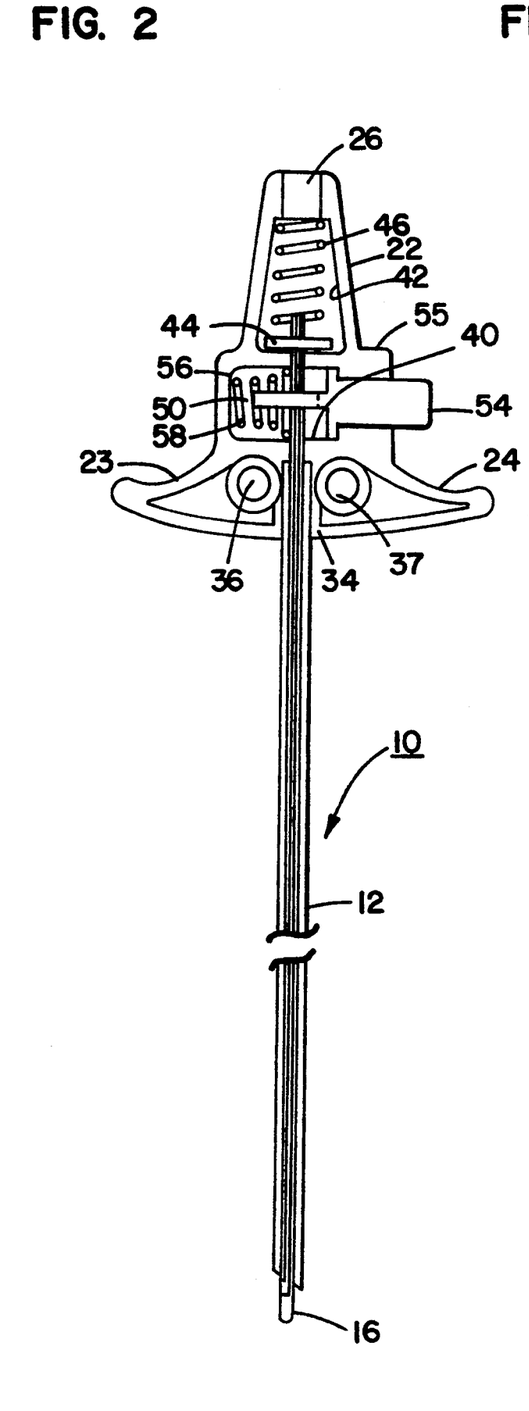
FIG. 2 is a front sectional view of the device of FIG. 1.
Figure 3:
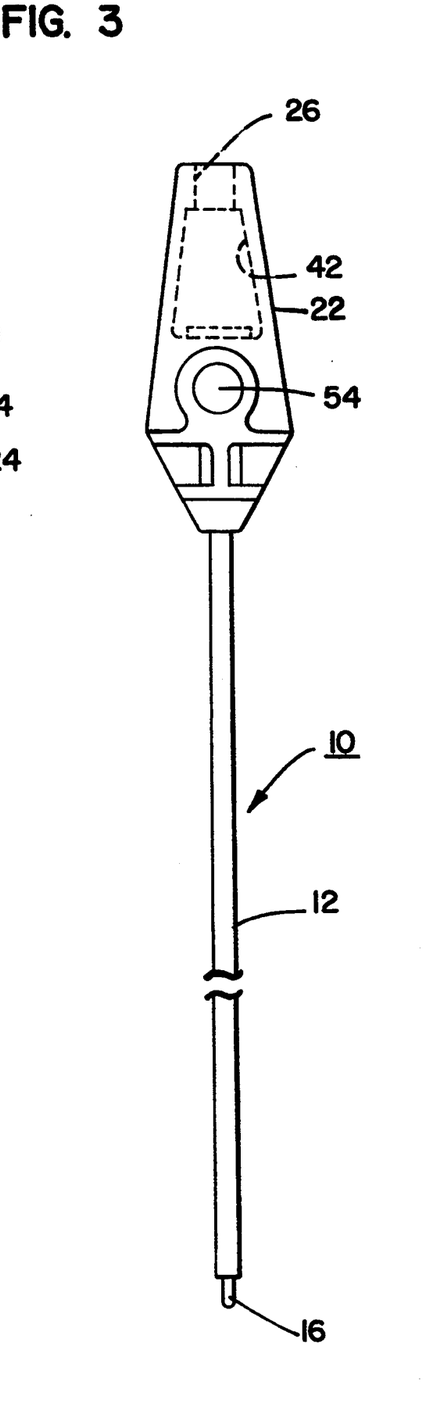
FIG. 3 is a side view of the device of FIGS. 1 and 2.

The proximal end of the cannula 12 is fixedly coupled to a handle 22 having side wings 23, 24 extending transversely to the central axis of the cannula 12 at its proximal end. The interior of the handle 22 is hollow, to communicate incoming gas delivered at an axial port 26 at the proximal end of the handle to the open interior end of the hollow obturator 16. A gas line 30, typically containing pressurized carbon dioxide, is coupled into the axial port 26 via a control valve 32 which is manually operable. A cannula bracket 34 about the central distal end of the handle 22 provides a seat for the proximal end of the cannula 12, about the central axis. The walls forming the seat for the cannula 12 lead, as seen in FIG. 2, tangentially to a pair of headbolts 36, 37 transverse to the side wings 23, 24 for holding split halves of the handle 22 together, one-half being shown in FIG. 2. This permits ready fabrication of the split halves by injection molding techniques, and rapid assembly of the functional interior elements before closure of the handle 22.

Adjacent the bolts 36, 37 at the proximal side is a wall 44 forming a lock chamber 40 through which the proximal end of the obturator rod 16 passes via wall apertures into an adjacent gas input pressure chamber 42 in communication with the axial port 26. A spring clip end 44 fitting transversely into a narrowed clip seat 45 (FIG. 6) adjacent the proximal end of the obturator rod 16 receives the spring clip 44, which is engaged by an axial compression spring 46 within the pressure chamber 42. The obturator rod 16 is biased under a spring force having a compliance, in this example, of approximately 2–4 pounds/inch. With this compliance, the obturator rod 16 is displaced over a short distance (⅛″ to ⅜″) by the resistance of encountered tissue such that its blunt tip 18 is withdrawn into the cannula 12 to expose the cutting end 14 of the cannula 12 at its distal end.

The mechanism in the lock chamber 40 (best seen in FIGS. 4 and 5) comprises a transverse lock element 50 lying in a plane transverse to the central axis and including an inset lock key opening 52 having walls spaced apart by a distance smaller than the diameter of the obturator rod 16, but leading to an interior key bore 53 that is larger in inner diameter than the outer diameter of the obturator rod 16. At one side of the lock chamber 40, a lock button 54 coupled to the lock element 50 extends sideways out from the side chamber wall 55, convenient to a surgeon or other manipulator of the Veress needle device 10. Near the opposite end of the lock element 50 from the lock button 54, a lock wing 56 in a plane parallel to the central axis is attached, to provide a movable base for a transverse compression spring 58 that extends between the opposite wall of the lock chamber 40 and the lock wing 56, biasing the button 54 in the direction out from the handle 22.

Figure 4:
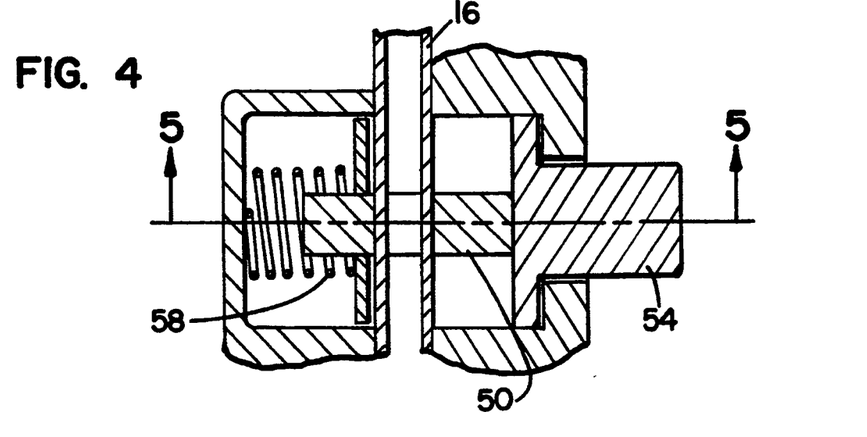
FIG. 4 is an enlarged fragmentary view of a portion of the arrangement of FIGS. 1-3, showing further details of a locking mechanism used therein.
Figure 5:
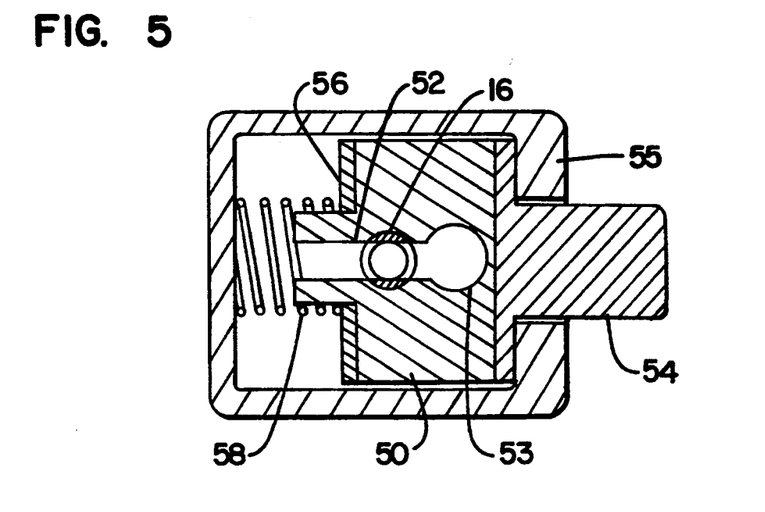
FIG. 5 is a top view of the sectional fragment of FIG. 4.
Figure 6:
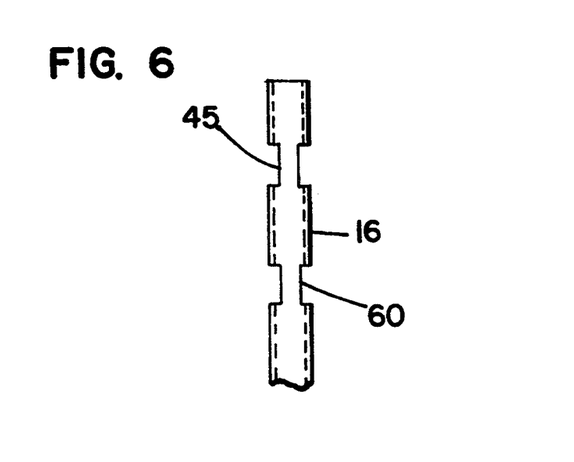
FIG. 6 is a fragmentary view of a portion of an obturator used in the devices of FIGS. 1-5.
Figures 7, 11:
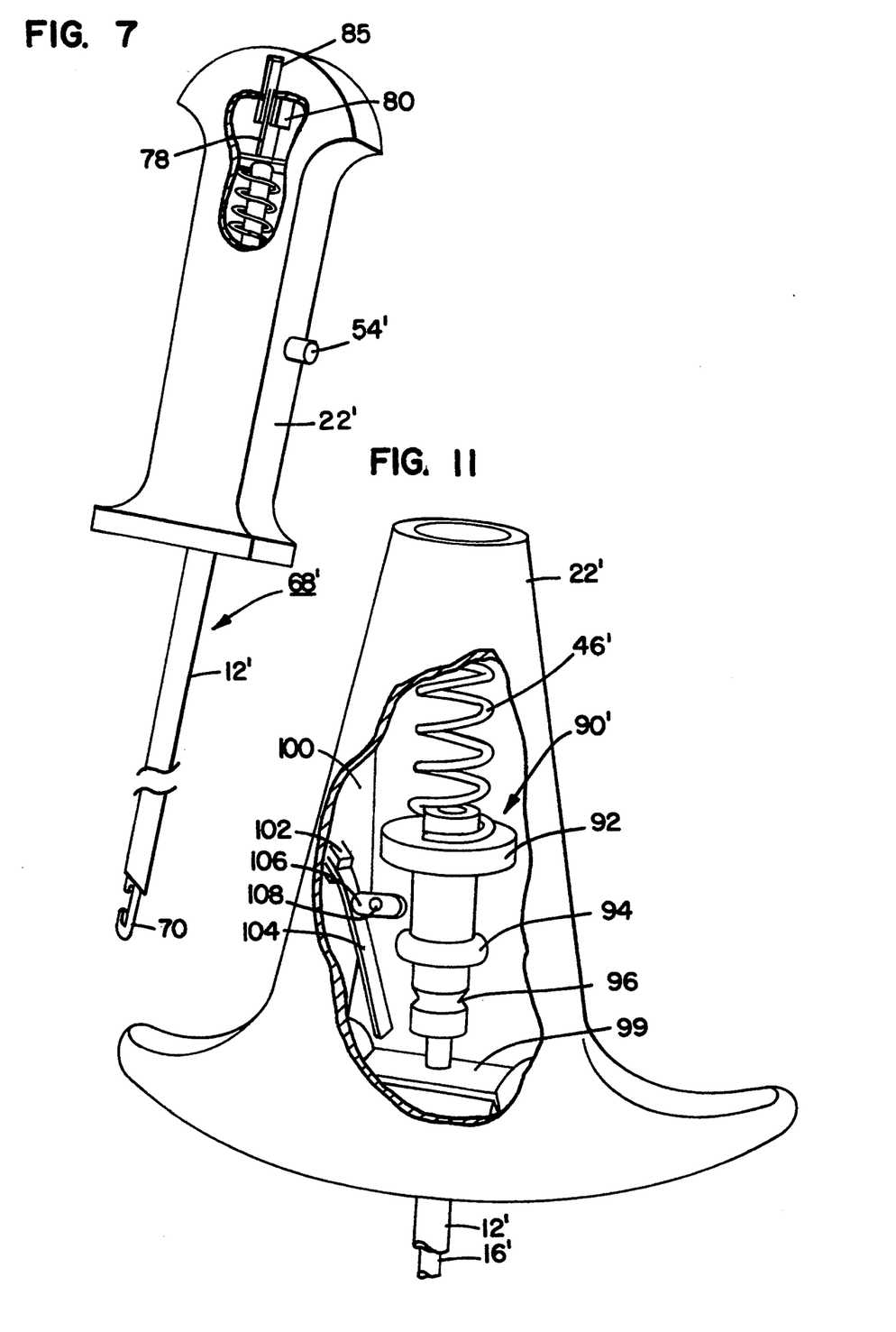
FIG. 7 is a perspective view, partially broken away, of a different form of safety device for laparoscopic instruments in accordance with the invention.
FIG. 11 is a perspective view, partially broken away, of a different form of safety device in accordance with the invention.
Figure 8:
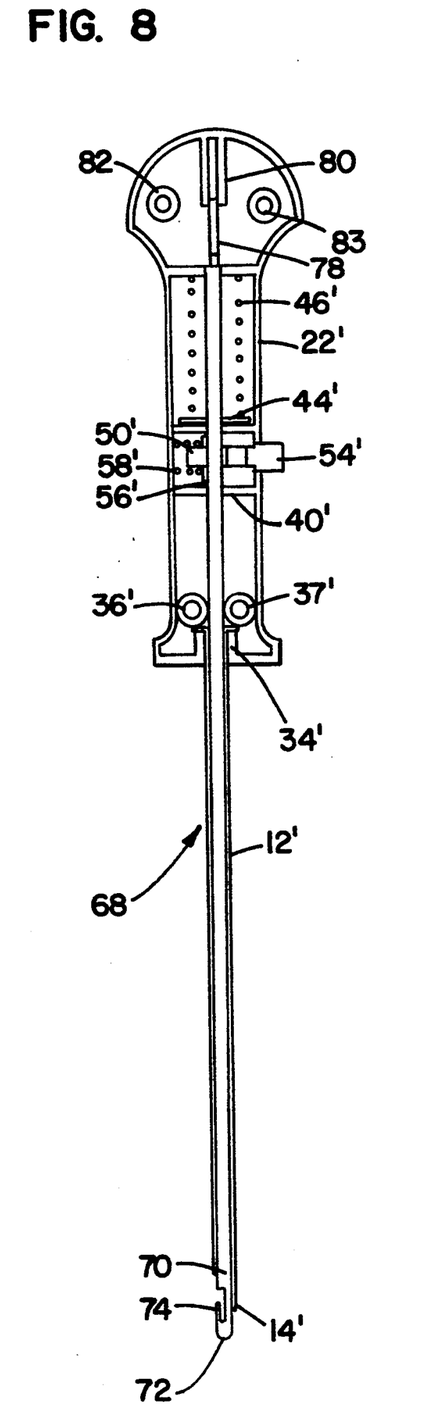
FIG. 8 is a front sectional view of the device of FIG. 7.
Figure 9:
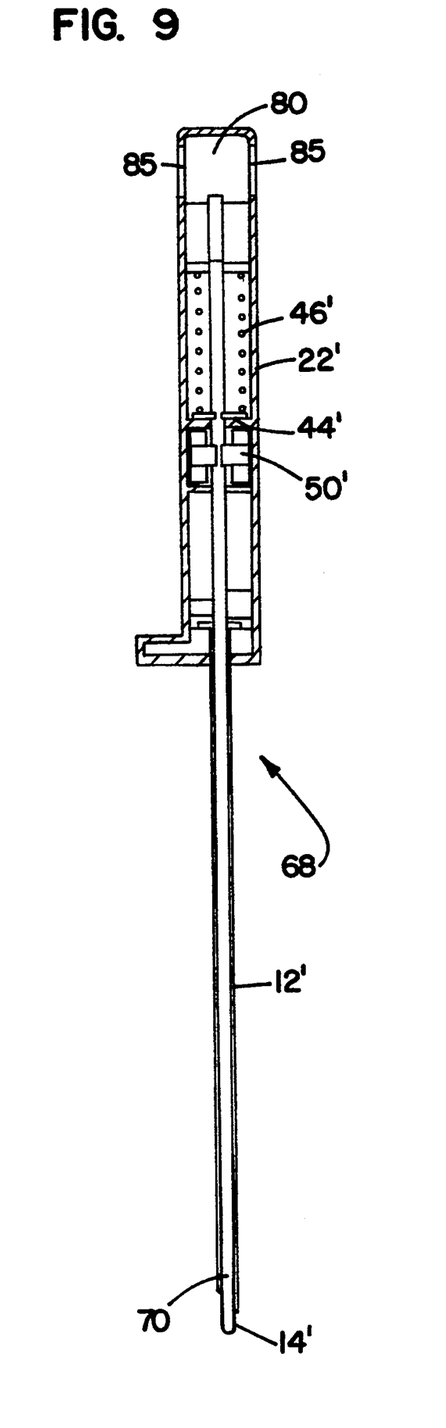
FIG. 9 is a side sectional view of the FIGS. 7 and 8.
Figure 10:
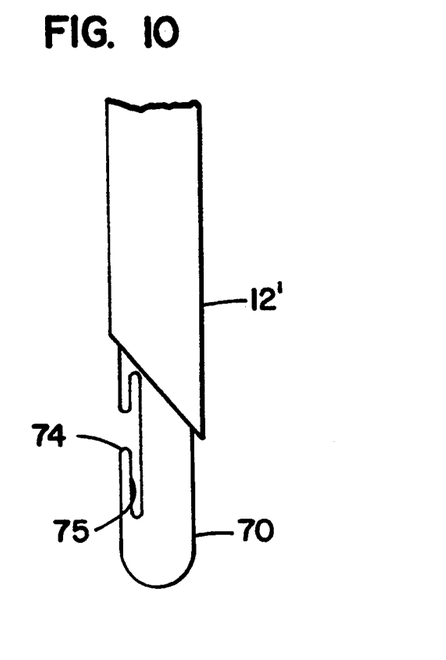
FIG. 10 is an enlarged fragmentary view of an example of a suture handling functional tip in a device in accordance with the invention.

As best seen in FIGS. 4–6, the obturator rod 16 also includes, spaced apart from its proximal end, an exterior narrowed inset region 60, which aligns with the lock element 50 when the distal end of the obturator rod 16 is at its distal limit position.

With this arrangement, the device 10 functions as a safety device while being used in the conventional manner for a Veress needle until penetration is complete. The obturator rod 16 is biased by the axial spring 46 to its extended distal position beyond the cutting end 14 of the cannula, being freed of the lock element 50 by the surgeon, who depresses the button 54 so that the obturator rod 16 is free to move axially within the key bore 53 of the lock element 50. Tissue and body wall resistance force the distal end of the obturator rod 16 back into the cannula 12, against the compliance of the spring 46, until the interior body cavity is reached, which fact is known to the surgeon because of substantially reduced resistance to insertion. At this point, the obturator rod is encountering no further resistance and the spring 46 forces it to its distal limit position. This position may be confirmed by inclusion of a transparent window (not shown) in the side of the handle 22 so that the location of the clip end 44 can be observed.

At this limit position, the inset region 60 in the obturator rod 16 is aligned with the key opening 52, so that the surgeon need only release the button 54. Thus, the transverse compression spring 58 forces the lock element 50 to its limit position, with the key opening 52 engaging the narrowed inset region 60 and locking the obturator rod 16 against axial movement. Consequently, once the distal end of the device 10 has entered the body cavity, the blunt tip 18 of the obturator rod 16 protects against the cutting end 14 of the cannula 12 engaging tissue or internal organs while exposed. The side aperture 20 in the obturator rod 16 is also unobstructed so that at this point, the control valve 32 in the gas line 30 may be opened. Gas pressure established in the chamber 42 is in communication through the hollow interior of the obturator rod 16 with the side aperture 20, to insufflate the body cavity. The side wings 23, 24 and the lock button 54 are conveniently sized and positioned for the surgeon, who achieves entry through the wall of the body in a conventional manner.

In other surgical procedures, it is advantageous to perform certain functions interior to the pneumoperitoneum after insufflation has been effected. A device for providing such a function is shown in FIGS. 7 to 10, to which reference is now made. This device comprises a suture retriever 68, and uses a number of parts and relationships substantially equivalent to those in the system of FIGS. 1–6. These elements therefore will be designated by similar numbers characterized by prime designations (′) and will not be described in detail. The cannula 12′ is seated in the distal end of the handle 22′, but the obturator comprises a central rod 70 of a length to have a blunt end 72 which at the distal limit position extends beyond the cutting edge 14′ of the cannula 12′. In this position, the exposed end of the concentric rod 70 includes an open-sided edge hook 74 (best seen in FIG. 10) having a narrow axial notch 75. The proximal end of the central rod 70 extends through the handle and through the axial compression spring 46 to a proximal end tab 78 or extension which is movable in a groove formed by a guideway 80 in the handle 22′. Upper head bolts 82, 83 secure the upper end of the handle 22′ together. A window 85 is provided in one or both of the front walls at the proximal end of the handle 22′, to permit visualization of the position of the tab 78 in the guideway 80. Inasmuch as this system is not gas pressurized, leakage is not a concern. Either an opening in the wall of the handle 22′ or transparent windows may be used.

As in the example of FIGS. 1–6, the surgeon depresses the control button 54′ in the device of FIGS. 7–10 to free the central obturator rod 70 as he inserts the suture retriever 68 in the body wall, allowing retraction of the blunt end 72 of the rod 70 and exposure of the cutting end 14′ of the cannula 12′ until the body cavity is reached. Thus, when the spring 46′ is again free to bias the rod 70′ to its distal limit position, the surgeon can release the control button 54′ based upon the minimal resistance to penetration and viewing the relative position of the proximal end tab 78 at its distal limit. Thereafter, the blunt end 72 of the obturator rod 70 shields the cutting edge 14′ of the cannula 12′, and the surgeon may insert the suture retriever 68 to a desired location, using the edge hook 74 and axial notch 75 to engage and retain a suture without danger of an inadvertent interior incision. This facilitates access by the surgeon into the pneumoperitoneum from locations and in directions that may either be planned or unanticipated, increasing the versatility with which the laparoscopic procedures may be carried out.

Some surgeons may prefer automatic locking and unlocking of the obturator rod, in contrast to the examples of FIGS. 1–6 and FIGS. 7–10, and this is accomplished by the arrangement of FIGS. 11–16. This safety device is shown as a Veress needle device, but it will be recognized that the principle is applicable to other safety devices as well. Again, a substantial number of elements are similar but may not be identical to the elements of the first example, so that the relationship is indicated by using prime (′) designations. For brevity, these like parts are not described in detail. The handle 22′ is again configured in a split fashion, the halves of which are secured together by head bolts 36′, 37′. The obturator rod 16′ reciprocates within the cannula 12′, but at its proximal end is coupled to an actuator sleeve 90 configured to provide a number of specific relationships. At its proximal end, the sleeve 90 includes a circumferential flange 92 providing a seat for the distal end of the axial compression spring 46'. In its mid-region, but closer to the distal end, the sleeve 90 includes a cam release ring 94 concentric about the central axis and serving a purpose described below. More closely adjacent its distal end, the sleeve 90 also includes a circumferential lock notch 96 used in securing the obturator rod 16' against axial movement. When the sleeve 90 reaches its distal limit it engages a transverse wall 99 in the handle 22'.

Figure 12:
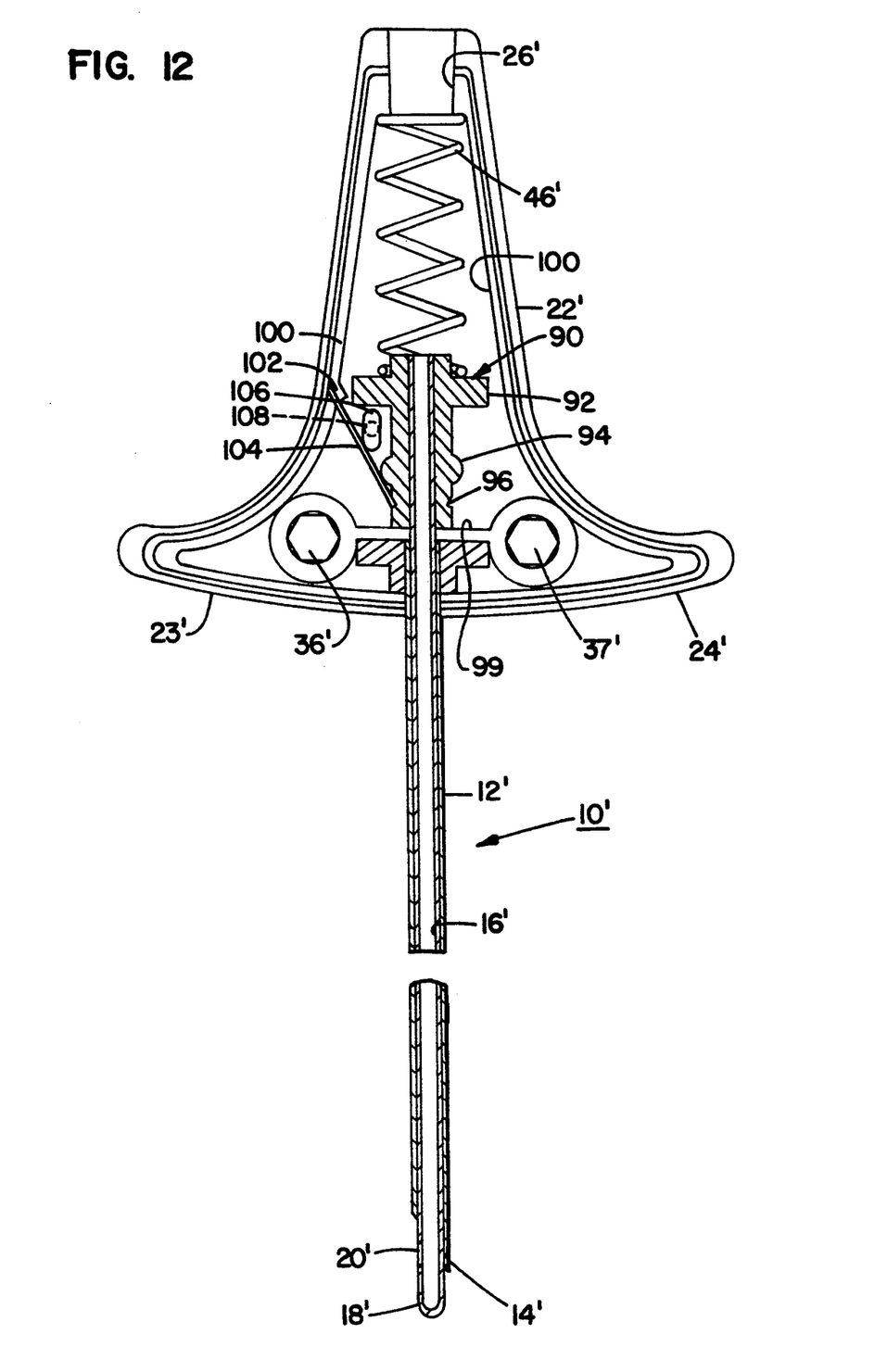
FIG. 12 is a front sectional view of the device of FIG. 11'.
Figure 13:
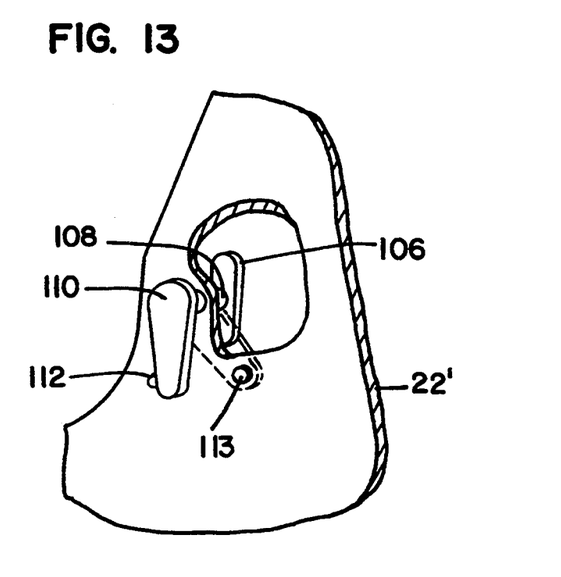
FIG. 13 is a fragmentary view, partially broken away, of the device of FIGS. 11 and 12, showing details of the control for the arming mechanism.

Within the periphery of the handle 22', as seen in FIG. 12, is a generally continuous interior wall 100 having a spring seat 102 within which a leaf spring 104 is mounted. The leaf spring 104 is angled in the direction toward the central axis, and slanted toward the surface of the actuator sleeve 90. In the mid-region of the leaf spring 104, between the leaf spring 104 and the actuator sleeve 90, is mounted a cam 106 on a cam shaft 108 that is rotatable in the housing 22 under control of an exterior handle 110 (FIG. 13). The handle 110 and interior cam 106 are rotatable through an approximately 45° angle, between a limit stop 112, and a detent 113 at the outside of the handle 22'.

Figure 14:
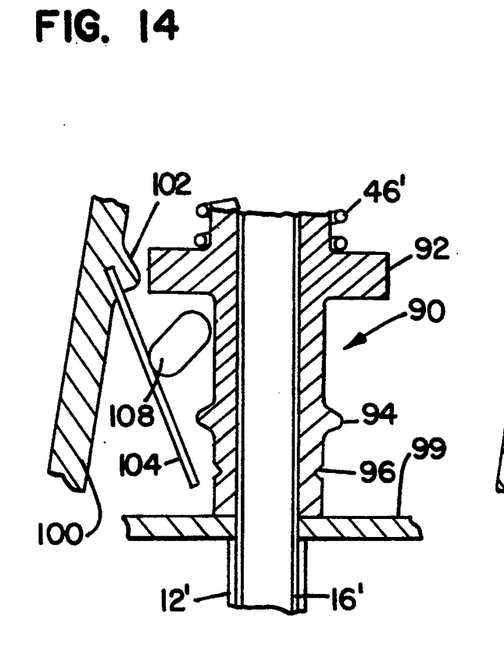
FIG. 14 is a side sectional fragmentary view of the device of FIGS. 11-13, showing the arming mechanisms in the armed position.
Figure 15:
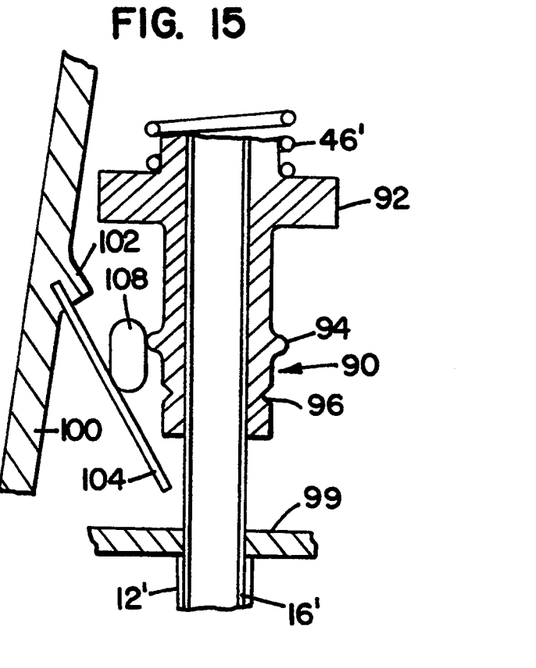
FIG. 15 is a view like that of FIG. 14, showing the arming mechanism displaced.
Figure 16:
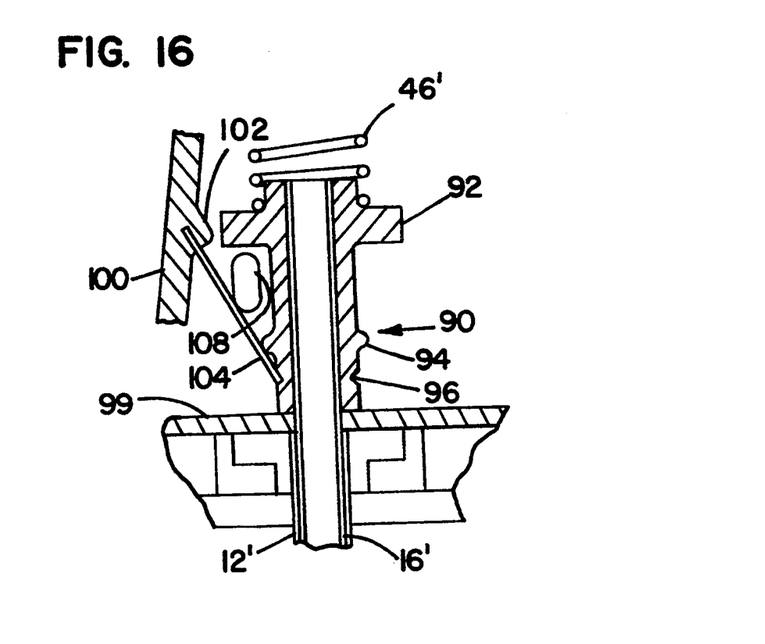
FIG. 16 is a view like that of FIGS. 13 and 14, showing the obturator rod locked in the distal limit position.

In operating the system of FIGS. 11-16, the surgeon arms the automatic locking mechanism by turning the control handle 110 so that the cam shaft 108 and cam 106 turn clockwise (as viewed but not shown in FIG. 12) to the limit position in which the handle 110 engages the detent 113 (FIG. 14). In the armed position, the leaf spring 104 is curved away from the actuator sleeve 90, into the position shown in dotted lines in FIGS. 11 and 14. The actuator sleeve 90 is free to move axially along the central axis, as the obturator 16' is forced proximally by the encountered body wall resistance. The obturator 16' moves toward the position in which the distal end 18' of the obturator 16' is interior to the cutting edge 14' of the cannula 12' as the body wall is penetrated. As the cam release ring 94 moves past the cam 106 during this withdrawal motion however, the cam release ring 94 engages the protruding projection on the cam 106 turning it counter clockwise to the position of FIG. 15. This action disarms the locking mechanism and allows the leaf spring 104 to assume the linear position shown in FIGS. 15 and 16. When the actuator sleeve 90 is returned to the distal limit by the force of the spring 46' when the cutting edge enters the body cavity, the tip of the leaf spring 104 seats in the circumferential lock notch 96, and the obturator rod 16' is thus fixed against any axial resistance encountered by the blunt tip 18'. Until this engagement, the actuator sleeve 90 is free to move up and down above the distal limit position, while the tip of the leaf spring 104 is below the distal end of the actuator 90. This requires only that the force of the axial spring 46 overcome the resistance of the leaf spring 104 and slightly bend it, over the final increment of movement, until the notch 96 is reached.

Figure 17:
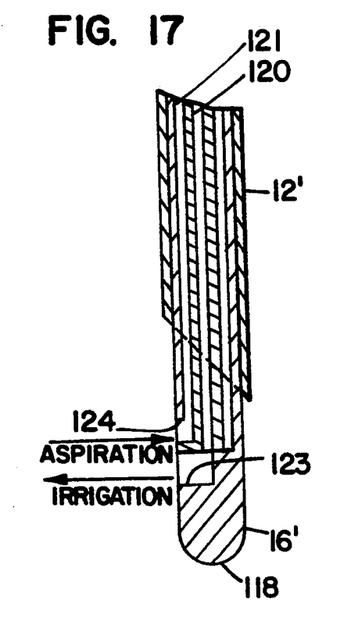
FIGS. 17, 18 and 19 are fragmentary side views of different functional tips for obturator rods in devices in accordance with the invention, depicting a suction/irrigation tip, a suture cutter tip, and a cauterizer tip, respectively.

Referring now to FIG. 17, another example of a functional tip for use in safety devices in accordance with the invention is intended for operation with, an irrigation/aspiration system. Here, the functional tip 118 comprises the blunt terminal end of dual concentric hollow conduits 120, 121 in the obturator rod, which includes two side apertures 123, 124, each communicating with a different conduit 120, 121, respectively. One conduit 121 is selectively coupled to a negative pressure source, for withdrawing or aspirating fluid, while the other conduit 120 is coupled to an irrigation source for providing a sterile fluid flow. Again, the blunt tip 118 of the obturator device is locked in the extended position after cutting entry has been accomplished. Alternatively, the irrigation aspiration system may have a single interior conduit, used for irrigation or aspiration in alternating fashion under surgeon control of a single value.

Figure 18:
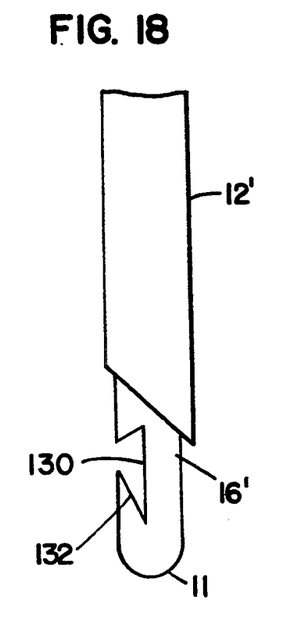

A different example of a suture handling functional tip is shown in FIG. 18 in which the obturator 16' has a blunt end 128 with an open sided notch 130. An angled interior surface 132 of the notch is a sharp cutting edge, whereby a suture may be engaged and cut.

Figure 19:
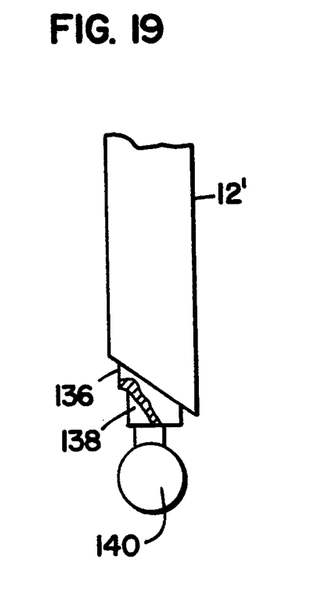

Yet another functional purpose is shown by a cauterizer tip, as shown in FIG. 19. The obturator includes an insulated exterior surface 136 and a conductive interior rod 138 which terminates in a conductive ball 140. On energization of a coupled voltage source by the surgeon, the ball tip 140 is energized to provide the cauterizing function. In other respects, it serves as previously described to protect against inadvertent incisions by the cutting edge of the cannula.

Although there have been described above and illustrated in the drawings, various forms and variants in accordance with the invention, it will be appreciated that the invention is not limited thereto but encompasses all modifications and expedients within the scope of the appended claims.

I claim:

1. A mechanism for controlling an obturator axially movable within a cutting cannula used for insertion into tissue forming part of a body wall, to permit proximal movement of the obturator during insertion and to lock the obturator in extended position when the cutting end of the cannula has cut through the body wall into a body cavity, to protect against inadvertent contact as surgical support functions are performed, comprising:

an obturator axially disposed and movable within the cutting cannula, the obturator having a length such that the obturator extends beyond the cutting end of the cannula in the distally locked position, and including a blunt tip and means adjacent the blunt tip for performing a surgical support function;

handle means coupled to the proximal end of the cannula, the handle means including first interior spring means engaging the obturator for biasing the obturator toward a distal position, and lock means, including second interior spring means, for engaging a proximal portion of the obturator to maintain the obturator in a distally locked position; and control means coupled to the handle means for disengaging the lock means from the obturator to allow axial movement of the obturator during insertion.

2. A mechanism as set forth in claim 1 above, wherein the lock means comprises a lock element transversely movable within the handle means to selectively disengage the obturator means while compressing the second spring means, and the control means comprises a control element exterior to the handle means and movable by an operator to move the lock element to the disengagement position.

3. A mechanism as set forth in claim 2 above, wherein the obturator includes a narrowed inset portion near its proximal end within the handle means, and wherein the lock element includes a slot engaging the inset portion in the engagement position of the lock element, and an aperture receiving the obturator element and allowing axial movement thereof in the disengagement position.

4. A mechanism as set forth in claim 3 above, wherein the handle means includes means defining an interior gas pressure chamber, and wherein the obturator comprises a hollow cylindrical member having a proximal end extending into the gas pressure chamber, and a side aperture adjacent the distal end of the obturator and in communication with the gas pressure chamber through the obturator the obturator extending beyond the cutting end of the cannula.

5. A mechanism as set forth in claim 3 above, wherein the obturator comprises a solid rod extending from within the handle means to a blunt end extending past the cutting end of the cannula when the obturator is in the distal position, the obturator including, at its proximal end, an extension member, and the handle means including an internal guideway adjacent its proximal end for receiving and guiding the extension member, the mechanism further includes window means for viewing the relative position of the extension member of the obturator means to the guideway.

6. A mechanism as set forth in claim 1 above, wherein the obturator comprises an elongated double sleeve element defining concentric fluid passageways within the obturator, the obturator having a blunt distal end including a pair of spaced apart apertures, each communicating with a different one of the conduits within the obturator.

7. A mechanism as set forth in claim 1 above, wherein the obturator comprises insulated conductive rod means having a cauterizer tip.

8. A mechanism as set forth in claim 1 above, wherein the obturator includes suture cutting means in the blunt tip.

9. A mechanism as set forth in claim 1 above, wherein the second spring means comprises means within the handle means for engaging the obturator to block axial movement when the obturator is at a distal limit position;
 arming means selectively controllable by an operator for maintaining the obturator free to move axially against the first interior spring means; and
 control means coupled to the obturator for disabling the arming means in response to movement of the obturator to a position adjacent the distal position.

10. A mechanism for controlling an obturator axially movable within a cutting cannula, to lock the obturator in position when the cutting end of the cannula has cut through a body wall into a body cavity, comprising:
 handle means coupled to the proximal end of the cannula, the handle means including first spring means engaging the obturator toward a distal position, including second spring means within the handle means for engaging the obturator to block axial movement when the obturator is at a distal limit position;
 arming means comprising cam means including a control lever exterior to the handle means and selectively controllable by an operator for forcing the second spring means to an armed position, for maintaining the obturator axially movable against the first spring means; and
 control means coupled to the handle means and comprising a cam shifter for returning the second spring means to a lock position for disabling the arming means in response to movement of the obturator to a position adjacent the distal position.

11. A safety laparoscopic instrument for insertion into a body cavity through a body wall and for effecting a surgical step therewithin, comprising:
 cannula means attached to the handle means and extending along a longitudinal central axis, the cannula means including a cutting distal end;
 obturator means disposed and reciprocal within the cannula means, the obturator means extending from within the handle means to a distal end which, when in a distal limit position, extends beyond the cutting end of the cannula means, wherein the side of the end of the obturator means includes means for performing a surgical step;
 means disposed within the handle means for biasing the obturator means toward the distal limit position with a compliance which yields to the resistance encountered when the instrument is passed through a body wall, such that the cutting end of the cannula is exposed for penetration through the body wall; and
 means selectively coupled to the obturator means within the handle means for locking the obturator means in the distal limit position with the side of the end of the obturator being exposed for performing a surgical step and the cutting distal end being shielded by the end of the obturator means.

12. An instrument as set forth in claim 11 above, wherein the means for locking the obturator means comprises means coupled to the handle means and engageable to the obturator means for automatically locking the obturator means at the distal limit position when that position is reached.

13. An instrument as set forth in claim 11 above, wherein the locking means comprises means including a control element accessible to a surgeon at the exterior of the handle means for maintaining the locking means disengaged until released by the surgeon.

14. A laparoscopic safety instrument for insertion into and use within a body cavity comprising the combination of:
 a cutting cannula comprising a hollow cylindrical element having a distal cutting edge;
 a surgical tool element disposed and reciprocal within the cannula, the tool element having a blunt distal end and tool instrument functional means adjacent thereto;
 handle means coupled to the cannula and coupled to the proximal end of the tool element for controlling the axial position thereof relative to the cannula, the handle means including first spring means for biasing the tool element axially toward a limit position in the distal direction with a first predetermined force which yields during insertion of the safety instrument, first lock means including second spring means for engaging the tool element at the distal limit position to prevent further axial movement, and second lock means controllable by an operator for maintaining the tool element subject to the first spring means until the limit position is reached under biasing force.

* * * * *